(12) United States Patent
Kole et al.

(10) Patent No.: US 10,539,504 B1
(45) Date of Patent: Jan. 21, 2020

(54) METHOD AND APPARATUS FOR AUTOMATING CONTACT BETWEEN AN ATR CRYSTAL AND A SPECIMEN

(71) Applicant: Agilent Technologies, Inc., Santa Clara, CA (US)

(72) Inventors: Matthew Kole, Santa Clara, CA (US); Andrew Ghetler, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 16/147,828

(22) Filed: Sep. 30, 2018

(51) Int. Cl.
*G01N 21/552* (2014.01)
*G01B 11/24* (2006.01)

(52) U.S. Cl.
CPC ....... *G01N 21/552* (2013.01); *G01B 11/2441* (2013.01)

(58) Field of Classification Search
CPC .......................... G01N 21/552; G01B 11/2441
USPC .................................................. 356/601, 445
See application file for complete search history.

(56) References Cited

U.S. PATENT DOCUMENTS 8,514,403 B2 * 8/2013 Ogawa ............... G01N 21/3581
356/496
9,863,877 B2 1/2018 Hoke 2011/0205528 A1 * 8/2011 Ogawa ............... G01N 21/3581
356/51

FOREIGN PATENT DOCUMENTS

EP 0819932 A1 1/1998
JP 2007 286147 A 11/2017

OTHER PUBLICATIONS

International Search Report, PCT/US2019/043297, dated Oct. 18, 2019.

* cited by examiner

*Primary Examiner* — Roy M Punnoose

(57) ABSTRACT

An ATR scanning system and a method for positioning a specimen against the reflective surface of an ATR objective are disclosed. The scanning system includes an ATR objective, a controller, a stage, and a height profiler. The controller forms an image of the reflective surface. The stage moves a specimen in a direction toward the reflective surface at a speed determined by the controller. The height profiler measures a minimum distance between the specimen and the reflective surface as the z-axis stage moves the specimen at a first speed. When the specimen is a predetermined distance from the reflective surface of the ATR objective, the controller causes the z-axis stage to move toward the reflective surface at a second speed while forming approach images of the reflective surface to determine if the specimen is in contact with the reflective surface.

13 Claims, 3 Drawing Sheets

METHOD AND APPARATUS FOR AUTOMATING CONTACT BETWEEN AN ATR CRYSTAL AND A SPECIMEN

BACKGROUND

Quantum cascade lasers provide a tunable mid-infrared (MIR) light source that can be used for spectroscopic measurements and images. Many chemical components of interest have molecular vibrations that are excited in the MIR region of the optical spectrum, which spans wavelengths between 2.5 to 25 microns. Hence, measuring the absorption of MIR light at various locations on a sample can provide useful information about the chemistry of the sample as a function of position on the sample.

One class of imaging spectrometers measures the light directly reflected from the sample as a function of position on the sample and wavelength of the illuminating MIR light. The amount of light that is reflected depends on both the chemical and physical attributes of the sample, since light can be lost both by absorption in the sample, which reflects the chemical composition of the specimen and by scattering, which depends on the physical state of the surface of the specimen. Hence, comparing spectra generated with direct reflection to absorption with known chemical absorption spectra that are available in libraries presents significant challenges.

Systems that utilize attenuated total reflection (ATR) to illuminate the specimen avoid the problems caused by scattering of the incident light by the specimen. For example, U.S. Pat. No. 9,863,877, issued Jan. 9, 2018 describes a scheme for scanning a portion of a specimen using ATR. These schemes reflect an incident light beam from a crystal surface at an angle that is less than the critical angle. The reflected light intensity is measured and compared to the incident light intensity to determine the absorption provided by a specimen that is in contact with the reflecting surface, but outside the crystal. While the light is totally reflected, the electric field generated by the light extends a few microns outside of the reflecting surface and can interact with the specimen. If the specimen absorbs light of the wavelength in the incident beam, the reflected light will be attenuated.

These schemes require that the specimen be brought within a few microns of the reflecting surface, and preferably, in contact with the reflecting surface. Problems arise when the specimen is either fragile or hard. The user must move the specimen such that the specimen touches the reflecting surface without forcing the specimen against the reflecting surface with sufficient force to damage either the specimen or the crystal. In practice, moving the specimen into position takes several minutes, and hence, limits the throughput of the spectrometer and requires significant operator skill to achieve the desired result.

SUMMARY

The present invention includes an ATR scanning system and a method for positioning a specimen against the reflective surface of an ATR objective. The scanning system includes an ATR objective, a controller, a z-axis stage, and a height profiler. The ATR objective is characterized by a reflecting surface from which light entering the ATR objective is totally reflected. The controller causes a light beam to enter the ATR objective and be focused to a point on the reflective surface such that the light beam is totally reflected from the reflecting surface at a position on the reflecting surface that is controlled by the controller. The controller forming an image of the reflective surface by measuring an intensity of light reflected from the reflecting surface at each of a plurality of different points on the reflective surface. The z-axis stage moves a specimen in a direction toward the reflective surface at a speed determined by the controller. The height profiler measures a minimum distance between the specimen and the reflective surface as the z-axis stage moves the specimen at a first speed.

In one aspect of the invention, the controller forms a background image of the reflective surface before the specimen is within a first distance of the reflective surface.

In another aspect of the invention, the controller causes the z-axis stage to move toward the reflective surface at a second speed while forming approach images of the reflective surface and comparing the images with the background image, the second speed being less than the first speed.

In another aspect of the invention, the second speed is less than 5 microns/second.

In another aspect of the invention, the controller stops the z-axis stage from moving further when one of the approach images indicates a region that is consistent with contact between the specimen and the reflective surface.

In another aspect of the invention, the controller verifies that the specimen is in contact with the reflective surface after the controller stops the z-axis stage.

The method of the invention automatically brings a specimen into contact with a reflecting surface of an ATR objective, while the specimen is mounted on a z-axis stage that moves the specimen in a direction toward the reflective surface under the control of a controller. The method includes moving the specimen toward the reflective surface at a first z-axis speed while measuring a distance between the specimen and the reflecting surface with a height profiler while the distance between the specimen and the reflective surface is greater than a first distance that is sufficient to ensure that the specimen will not contact the reflective surface. After the specimen is positioned closer to the reflective surface than said first distance, the z-axis distance is repeatedly stepped by an approach step size and a first image of the reflective surface formed until the first image indicates that the specimen is in contact with the reflective surface.

In one aspect of the invention, the first image is formed by measuring an attenuation of light of a predetermined wavelength after the light is reflected from the reflective surface as a function of position on the reflective surface.

In another aspect of the invention, the first image is compared to a second image of the reflective surface when the specimen is not contacting the reflective surface to determine if the specimen is in contact with the reflective surface.

In another aspect of the invention, the reflective surface is configured to reflect light of a predetermined wavelength, wherein an electric field generated by the light reflecting off of the reflective surface extends by a first distance from the reflective surface toward the specimen, and wherein the approach step size is less than the first distance.

In another aspect of the invention, the approach size is less than 5 microns.

In another aspect of the invention, the approach size is less than 3 microns.

In another aspect of the invention, the approach size is less than 1 micron.

DETAILED DESCRIPTION

Figure 1:
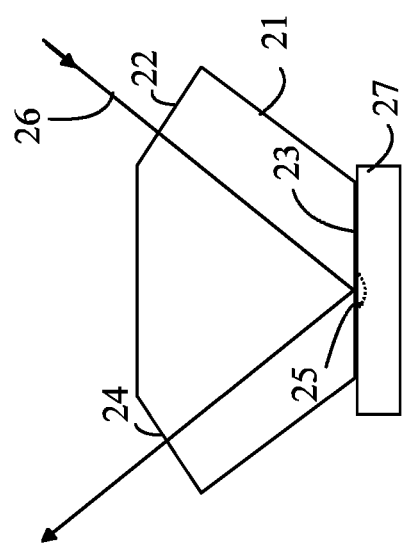
FIG. 1 illustrates a simple ATR optical system that is attached to a specimen.

The manner in which the present invention provides its advantages can be more easily understood with reference to FIG. 1, which illustrates a simple ATR optical system that is attached to a specimen. FIG. 1 is a cross-sectional view of an interface crystal that can facilitate the measurement of the absorption of light by a sample 27 in the reflective geometry mode. Crystal 21 has a high index of refraction. Light beam 26 enters crystal 21 through port 22 and strikes facet 23 at an angle that is greater than the critical angle. The light beam is totally reflected from facet 23 and exits the crystal through port 24. At the point at which the light beam is reflected from facet 23, the electric field associated with the light beam extends outside the crystal as shown at 25. If the medium under facet 23 absorbs light at the wavelength of light beam 26, the evanescent field will interact with the medium and energy will be transferred from the light beam to the medium. In this case, the energy in the beam leaving crystal 21 will be reduced. The difference in intensity between the input and output beams as a function of wavelength is a spectrum that matches a high-quality transmission spectrum and can easily be used for matching conventional spectra for various chemical compounds.

While an interface crystal of the type discussed above is useful in measuring a MIR spectrum of a point on a sample, it presents challenges if an image of an area on the specimen is needed, particularly if the surface of the specimen is not smooth. To form an image, the interface must be moved relative to the specimen. To prevent the interface crystal from damaging the specimen, the specimen must be moved vertically to allow the crystal to be located at the next point of interest. The time for such point-to-point measurements makes a combination imaging and spectrometer instrument impractical unless very long times are available to generate a spectrum at each point on a specimen in high resolution.

Figure 2:
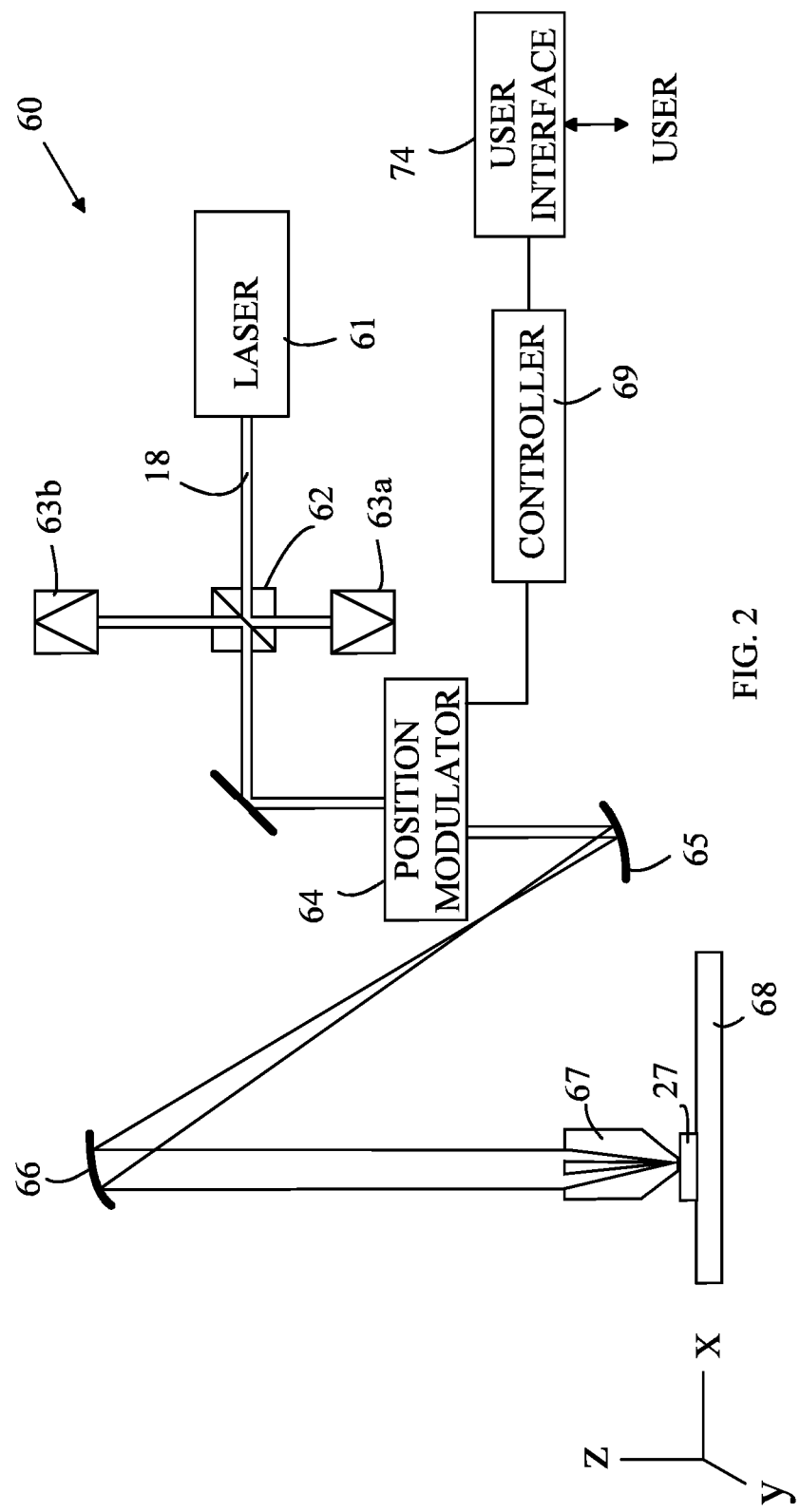
FIG. 2 illustrates a scanning ATR system in which the present invention can be practiced.

The above-described US Patent teaches an ATR measurement system in which the point of interaction of the input light beam can be rapidly scanned across the specimen without the need to move the crystal. Refer now to FIG. 2, which illustrates a scanning ATR system 60 in which the present invention can be practiced. Light 18 from laser 61 is split by beam splitter 62 into two beams. The first beam is directed to detector 63a, which measures the intensity of the laser pulse. The second beam is directed to position modulator 64 which adjusts the point of illumination of the beam on an off-axis parabolic reflector 65. The position of illumination determines the position at which the light from parabolic reflector 65 strikes a second off-axis parabolic reflector 66. Parabolic reflector 66 re-collimates the beam and sets the diameter of the beam to match the input aperture of ATR objective 67. The inclination of the beam entering ATR objective 67 is determined by the point of illumination on parabolic reflector 65. The light reflected back by ATR objective 67 retraces the path of the incoming light and a portion of that light is directed by beam splitter 62 into detector 63b. Controller 69 can then determine the amount of light that was lost in the reflection from ATR objective 67, and hence, determine the amount of light absorbed by sample 27. To image another small area on sample 27, controller 69 operates a three axis stage 68.

Many specimens of interest have irregular surfaces. The resulting height variations are often much greater than the depth of the electric field at the reflection surface in the ATR objective. As noted above, the effective depth of the field below the reflection surface of the ATR objective is a few microns. Hence, unless the surface variations are less than a few microns, or the sample is compressible, when the objective is brought into contact with the specimen there are isolated points of contact that, typically, cannot be predicted in advance.

For the purposes of this application, a specimen will be defined to be in contact with a specimen at a location on the reflecting surface when the light absorbed from the reflecting beam is distinguishable from the noise in measuring the attenuation of the reflecting light beam. Hence, "contact" can include the specimen being within one or two wavelengths of the light beam from the actual reflecting surface.

The present invention utilizes a two-phase process for bringing the sample into contact with the ATR objective. In the first phase, the stage on which the sample is mounted is moved in the direction of the ATR objective in large/fast steps while the distance between the sample and the ATR objective is estimated using an optical profiling estimator. Once the sample is within a predetermined distance from touching the ATR objective, the step size/rate of travel is reduced substantially and images of the sample as seen by the ATR objective are used to determine when the sample is just touching the reflecting surface of the ATR objective while the stage is still moving.

Figure 3:
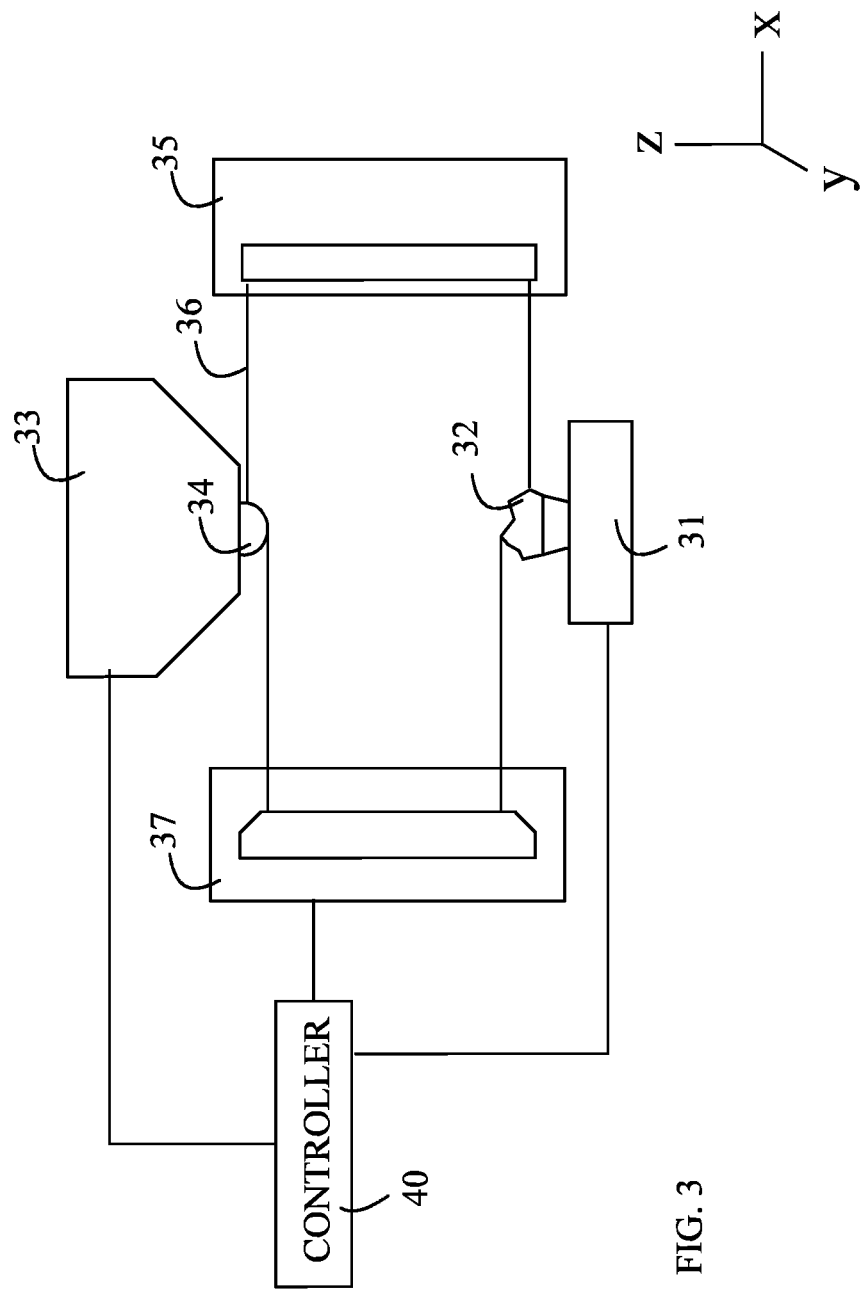
FIG. 3 illustrates one embodiment of an optical profiling estimator that can be used with the present invention.

Refer now to FIG. 3, which illustrates one embodiment of an optical profiling estimator that can be used with the present invention. The sample 32 is mounted on a stage 31 which moves the sample in the Z direction under the control of controller 40. The stage movement allows the sample to be brought closer to the reflecting surface 34 of ATR objective 33. The optical profiler includes a light source 35 which generates a collimated light beam 36 that illuminates the space between the specimen and the reflecting surface 34 and casts a shadow of the sample and the ATR objective reflecting surface onto an imaging array 37. As the stage moves the sample closer to the ATR objective, the amount of light reaching imaging array 37 decreases. When the sample is close to the ATR objective, but still at a safe distance, the controller switches to the second phase of the positioning method. In the first phase, a series of discrete measurements are made covering a range of approximately 2 mm-0.5 mm from the crystal. These measurements are used to rapidly estimate the contact position between the crystal and the specimen. The optical profiler does not have perfect accuracy; thus, the disagreement between these measurements indicates how accurate the profiler is, and allows an appropriate stopping distance for this first phase to be determined.

Once the stage has moved the specimen to within a predetermined distance from the reflecting surface, the imaging system is used to further position the specimen using a slower rate of motion. As noted above, the evanescent field from the reflected light beam extends a few microns below the surface of the ATR objective. As a result, an image of the reflecting surface will begin to show areas of absorption before the specimen actually contacts the reflecting surface. Differentiating the areas of "near" contact from noise poses challenges when the surface of the specimen just begins to absorb light from the reflecting beam.

To measure the absorption, the system must "know" the incident light intensity on the reflecting surface of the ATR objective crystal at the point at which the light is focused.

The electric field in the specimen is only a few microns deep; hence, the amount of material being exposed is quite small. The optical path from the laser to the specimen is many centimeters, and hence, any absorber in that path can alter the intensity by an amount that is significant when compared to the light actually absorbed by the specimen.

The optical path between beam splitter 62 and ATR objective 67 is not a vacuum. The light must pass through a gaseous environment that has absorption bands in the MIR. Those absorption bands reduce the light that reaches the reflecting surface of the ATR objective and also the light that is returned from the surface. For example, the path typically includes some level of water vapor. The water vapor absorption is a function of wavelength and temperature. These variations can vary over short periods of time, and hence, need to be calibrated immediately prior to any scan of absorption as a function of frequency.

In one aspect of the invention, a background image of the reflecting surface is formed at the particular wavelength that will be used in determining when the specimen is close to the reflecting surface. The background image is formed when the specimen is sufficiently removed from the reflecting surface to ensure that the image does not reflect absorption by the specimen. As the specimen is moved closer to the reflecting surface, images of the reflecting surface are continually formed and compared to the background image. When the specimen is within a few microns of the surface, the specimen will begin to absorb light from the electric field generated by the reflected light that extends below the reflecting surface.

It is advantageous to prevent images of the surface generated by noise from being interpreted as absorption from the specimen when the specimen is far from the reflecting surface. In one aspect of the invention, spatial filtering is utilized to distinguish such false positives from images of a portion of the specimen. In one embodiment, image features that are less than a predetermined size are rejected. For example, image features that are less than 2 pixels are rejected. In another embodiment, image features that fluctuate positive and negative with respect to the background image in a sequence of successive frames are rejected.

When an image feature that is not noise and has a spatial extent consistent with a region of contact, or near contact, is found, the motion in the Z-direction stops and three successive images are taken in sequence. If the image feature that caused the motion to be stopped is the result of the specimen coming in contact with the reflecting surface, the image feature will have substantially the same intensity and position in all three images. If this is not the case, the slow approach motion is resumed, and the process is repeated.

In one embodiment, the rate of motion in the second phase is adjustable, and occurs in discrete steps of either 1 um, 3 um (default/recommended) or 5 um. The second phase is implemented in discrete steps. The z-axis stage steps by the chosen step and an image is formed. The step and image require about 1 second. At the recommended step size, the second phase positioning moves at about 3 microns/sec. The lower step size option is used for very fragile specimens or specimens with small features. The higher step size option is used for more robust specimens that are less susceptible to being damaged.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An ATR scanning system comprising:
   an ATR objective characterized by a reflective surface from which light entering said ATR objective is totally reflected;
   a controller that causes a light beam to enter said ATR objective and be focused to a point on said reflective surface such that said light beam is totally reflected from said reflecting surface at said point, said point being controlled by said controller, said controller forming an image of said reflective surface by measuring an intensity of light reflected from said reflecting surface at each of a plurality of different points on said reflective surface;
   a z-axis stage that moves a specimen in a direction toward said reflective surface at a speed determined by said controller; and
   a height profiler that measures a minimum distance between said specimen and said reflective surface as said z-axis stage moves said specimen at a first speed.

2. The ATR scanning system of claim 1 wherein said controller forms a background image of said reflective surface before said specimen is within a first distance of said reflective surface.

3. The ATR scanning system of claim 2 wherein said controller causes said z-axis stage to move toward said reflective surface at a second speed while forming approach images of said reflective surface and comparing said images with said background image, said second speed being less than said first speed.

4. The ATR scanning system of claim 3 wherein said second speed is less than 5 microns/second.

5. The ATR scanning system of claim 3 wherein said controller stops said z-axis stage from moving further when one of said approach images indicates a region that is consistent with contact between said specimen and said reflective surface.

6. The ATR scanning system of claim 5 wherein said controller verifies that said specimen is in contact with said reflective surface after said controller stops said z-axis stage.

7. A method for automatically bringing a specimen into contact with a reflecting surface of an ATR objective, said specimen being mounted on a z-axis stage that moves said specimen in a direction toward said reflective surface by a controller, said method comprising:
   moving said specimen toward said reflective surface at a first z-axis speed while measuring a distance between said specimen and said reflecting surface with a height profiler while said distance between said specimen and said reflective surface is greater than a first distance that is sufficient to ensure that said specimen will not contact said reflective surface; and
   repeatedly stepping said z-axis stage by an approach step size and forming a first image of said reflective surface when said specimen is closer than said first distance until said first image indicates that said specimen is in contact with said reflective surface.

8. The method of claim 7 wherein said first image is formed by measuring an attenuation of light of a predetermined wavelength after said light is reflected from said reflective surface as a function of position on said reflective surface.

9. The method of claim 8 wherein said first image is compared to a second image of said reflective surface when said specimen is not contacting said reflective surface to determine if said specimen is in contact with said reflective surface.

10. The method of claim 7 wherein said reflective surface is configured to reflect light of a predetermined wavelength, wherein an electric field generated by said light reflecting off of said reflective surface extends by a first distance from said reflective surface toward said specimen, and wherein said approach step size is less than said first distance.

11. The method of claim 7 wherein said approach size is less than 5 microns.

12. The method of claim 7 wherein said approach size is less than 3 microns.

13. The method of claim 7 wherein said approach size is less than 1 micron.

* * * * *